US006403301B1

(12) United States Patent
Ludwig et al.

(10) Patent No.: US 6,403,301 B1
(45) Date of Patent: Jun. 11, 2002

(54) PROCESS FOR DETECTING BORNA DISEASE VIRUS (BDV) INFECTIONS

(76) Inventors: Hans Ludwig; Liv Bode, both of Beerenstrasse. 41, D-14163 Berlin (DE)

( * ) Notice: Subject to any disclaimer, the term of this patent is extended or adjusted under 35 U.S.C. 154(b) by 0 days.

(21) Appl. No.: 09/582,615
(22) PCT Filed: Dec. 24, 1998
(86) PCT No.: PCT/DE98/03793
§ 371 (c)(1), (2), (4) Date: Nov. 28, 2000
(87) PCT Pub. No.: WO99/34216
PCT Pub. Date: Jul. 8, 1999

(30) Foreign Application Priority Data

Dec. 29, 1997 (DE) .......................................... 197 58 017

(51) Int. Cl.[7] .......................... C12Q 1/70; A61K 39/42; A61K 39/395

(52) U.S. Cl. .......................... 435/5; 422/61; 424/159.1; 424/141.1

(58) Field of Search .............................. 435/5; 422/61; 424/159.1, 141.1

(56) References Cited

U.S. PATENT DOCUMENTS 4,551,435 A * 11/1985 Liberti et al. ............... 436/541
5,122,112 A * 6/1992 Jones ............................ 604/4
5,556,744 A * 9/1996 Weiner et al. ................. 435/5
5,654,401 A 8/1997 Clements et al. ........... 530/350

OTHER PUBLICATIONS

Bode et al., *Molecular Psychiatry*, 6:481–491 (2001).
Briese et al., "Enzyme–Linked Immunosorbent Assay for Detecting Antibodies to Borna Disease Virus–Specific Proteins", J. of Clin. Microb., vol. 33, No. 2, pp. 348–351, (1995) XP–000571175.

Stitz et al., "Borna Disease in Rhesus Monkeys as a Model for Uveo–Cerebral Symptoms", J. of Med. Virology, 6:333–340, (1980), XP–002103967.

U.E. Nydegger in R. F. Masseyeff (aa), "Methods of Immunological Analysis", VCH Verlagsgesellschaft, Weinheim (a a), vol. 1, pp. 646–656, (1993).

Deuschle et al., "Borna disease virus proteins in cerebrospinal fluid of patients with recurrent depression and Multiple sclerosis", The Lancet, vol. 352, pp. 1828–1829, (1998).

J. Carlos de la Torre et al., "Sequence characterization of human Borna disease virus", Virus Research 44, pp. 33–44, (1996).

(List continued on next page.)

*Primary Examiner*—Hankyel T. Park
*Assistant Examiner*—Stacy S. Brown
(74) *Attorney, Agent, or Firm*—Foley & Lardner

(57) ABSTRACT

The invention allows, for the first time, to (almost) perfectly detect the various phases of a BDV infection in all species by combining a newly discovered test parameter, the circulating immune complexes (CICs) in the blood plasma, with already known parameters, antigen (AG) in white blood cells and antibodies (AK) in the plasma. All three parameters can be determined from a single blood sample. The detection of BDV-specific CICs described for the first time by the invention as the only infection markers with long-time persistence allows both the detection of healthy carriers (latent infections) and the evaluation of the development of the infection and of therapy results in the case of diseased individuals.

26 Claims, 7 Drawing Sheets

OTHER PUBLICATIONS

H. Ludwig et al., "Biology and neurobiology of Borna disease viruses (BDV), defined by antibodies, Neutralizability and their pathogenic potential", Arch Virol. [Suppl] 7, Springer Verlag, pp. 111–133, (1993).

Data bank: Medline at STN, AN 97339570, AB. (T. Horimoto; (a. a.), Journal of Clinical Microbiology, vol. 35, No. 7, pp. 1661–1666) 1997.

Data bank: Medline at STN, AN 92251347 AB.. (L. Bode (a. a.), Jounal of Medical Virology, vol. 36, No. 4, pp. 309–315) 1992.

Data bank: Medline at STN, AN 91247177, AB (I. Bause–Niedrig, (a. a.), Veterinary Immunology and Immunopathology, vol. 27, No. 4, pp. 293–301) 1991.

Data bank: CA at STN, AN 122:157916, AB. (Briese (a. a.), J. Clin. Microbiol., vol. 33, No. 2, pp. 348–351, 1995.

* cited by examiner

PROCESS FOR DETECTING BORNA DISEASE VIRUS (BDV) INFECTIONS

FIELD OF THE INVENTION

The invention relates to a process for detecting BDV infections via detecting immune complexes which circulate in body fluids (CICs), a process for detecting CICs in general, in particular BDV-specific CICs, and to a diagnostic kit which is suitable for these detection processes.

BACKGROUND OF THE INVENTION

BDV infections are found in a large number of livestock and domestic animals (horses, sheep, cattle, cats) and in humans. BDV is a coated virus of 90 nm diameter with a genome of unsegmented single-stranded RNA of negative polarity which encodes 5 genes (genome size: 8.9 kilobases). Related viruses include, for example, the rabies virus and the measles virus. Owing to genetic particularities (replication in the nucleus of the host cell), BDV is classified as the prototype of a separate family of viruses (Bornaviridae). BDV has a particular preference for the nerve cells in the limbic system of the brain, a functional unit in which behavior, emotions and memory functions are controlled. However, other cell types are also attacked by BDV. Peripheral mononuclear leukocytes (PBMCs) are of particular diagnostic importance. BDV does not destroy the host cells (no cytopathogenic effect), neither in the host (in vivo) nor in cell culture (in vitro). The primary pathogenic effect of BDV is based on a functional disturbance in the infected brain cells which is probably induced by interaction with neurotransmitter receptors. Experimental data obtained on animals suggest that glutamate receptors are (reversibly) blocked. The exact mechanism and the receptor type are as yet unknown.

In animals, BDV infections are associated with periodic behavioral disorders with the indicating signs listlessness, hypoprosexia and ataxia. In humans, infectious human Bornaviruses have been isolated from patients with recurrent endogenous affective disorders, and it is highly likely that they are involved in these disorders and possibly other disorders of the cerebral function (also presumably via neurotransmitter functions). Endogenous recurrent depressions, including the manic-depressive form, account for 1–5% of the important psychiatric diseases and are a considerable health problem owing to the severity of the disablement, not only for the sufferers, but, from the socio-economical angle, also for society.

BDV infections persist in animals and humans, probably for life. The sources of the infection remain entirely unknown. The course of the infection is distinguished by latent and activated phases. During the activated phases, clinical symptoms can occur. In animals (horses are the most investigated species), a number of infections without disease exist (asymptomatic carriers). This percentage can amount to up to 50% in a group of horses in which an illness was identified. The danger of an intense, disease-associated activation phase of the infection depends on genetic factors and the stress of the individual (stress factors, immunosuppression).

In humans, there is probably no general risk of illness for healthy infected individuals which are not predisposed to affective disorders. In contrast, an increased risk of disease by BDV infection in the narrower sense exists in individuals with a predisposition of developing an affective disorder, in individuals where an affective disorder is already clinically apparent, and in as yet healthy first-degree relations of these individuals.

There is an indisputable increasing demand for reliable diagnostic systems for identifying BDV infection, not only in asymptomatic carriers (for epidemiological reasons), but also for monitoring the infection phases in diseased individuals.

Conventional antibody tests are known since the BDV virus has already been studied thoroughly and is already fully sequenced. Until 1993, an antibody test in the serum was the only possibility. As a rule, antibodies are directed against the BDV nucleoprotein p40 (relative molecular weight 40 kDa) and against the phosphoprotein p24 (24 kDa). These antibodies do not neutralize the virus. It soon emerged that the lack of specific antibodies did not exclude infection with BDV. This means that the antibodies do not persist in the serum of the infected individual, or not for a very long time. Moreover, the Ab concentrations (titers) in naturally infected humans and animals are only low in the first place and cannot always be identified with less sensitive test systems.

Important progress, in particular for assessing disease-relevant activations of the BDV infection, was made by the discovery that PBMCs express viral proteins which can be detected in cells after disrupting the latter. These proteins are occasionally also found in the plasma. Protein (AG) expression has proved to be the decisive activity parameter. It correlates well with clinical disease (humans and animals), can be quantified and is of great importance for assessing the further pathogenesis (chances of recovery, response to antidepressants and the like). Also, AG determination cannot be replaced by detecting viral nucleic acid in the PBMCs via amplification with nested RT PCR, since it is only the virus itself which is detected by this method, but no information can be obtained on its current or, possibly, future activity.

As a rule, the AG marker is limited to part (2–3 weeks) of the acute disease phase and can no longer be detected during convalescence. Thereafter, the Ab may be detectable intermittently, depending on the severity of the activation episode, but they may also be completely absent.

This current state of BDV diagnostics fails especially during convalescence, during the symptom-free interval (which may last for years) of a patient (humans and animals) and in infected individuals which are as yet disease-free, i.e., in brief, in the case of BDV infections in the latent stage. Both test parameters, with AG and Ab, can give erroneous negative results during the latent phase, even though the infection continues to exist.

*Journal of Clinical Microbiology*, 1997, vol. 35, no. 7, pp. 1661–1666, Horimoto, T. et al. (via MEDLINE TO 97339670) describes an ELISA test for detecting BDV-specific antibodies in which microwell plates were coated with BDV p40 antigen in order to catch and detect antibodies specific for this BDV nucleoprotein. It was found that many specimens which had previously been assayed differently and were found to be seropositive gave a negative result with regard to the antibodies. It was concluded that the other studies would have contained a high percentage of erroneously positive results. However, the results also allowed the conclusion that BDV infections cannot be detected in each individual case via the antibody titer. Thus, an overall diagnostic approach seems to be required.

It was therefore the object of the invention to develop a novel detection process for the infection to allow as complete a detection as possible of BDV infections, which, owing to their persistence, can last for very long periods, with acute and latent phases alternating. Also, it was intended to provide a diagnostic kit which can be used for such a detection.

SUMMARY OF THE INVENTION

To achieve this object, the invention provides a process for detecting Borna disease virus (BDV) infection, in which immune complexes of BDV antigens and specific antibodies attached thereto, which circulate freely in the body fluid, are detected in a body fluid specimen to be tested by means of a suitable immunological assay. An essential aspect of the invention is therefore based on the finding that high concentrations of circulating immune complexes composed of BDV antigens and antibodies against them which are formed specifically by the body occur in body fluids, for example in blood serum, during certain phases of the disease. These immune complexes can also be present in particular during precisely those disease phases during which antigens and/or antibodies cannot be detected.

In principle, the existence of immune complexes, i.e. complexes composed of antigens and antibodies and which are freely mobile in the blood, is already known, but the relevance of these complexes differs greatly for each individual case.

For example, NYDEGGER, U. E., in: MASSEYEFF, R. F. [inter alia] [Editor].: "Method of Immunological Analysis", VCH Verlagsgesellschaft, Weinheim [inter alia] 1993, Vol. 1, pp. 646–656 discloses an ELISA assay for HIV-specific CICs. The authors found high levels of circulating immune complexes in HIV-positive drug addicts. They state that approximately one tenth of all of the serum IgG present was complexed in CICs. Accordingly, the importance of the CICs is obviously virus-specific. In the case of BDV infections—and in some cases also in HIV infections—the percentage of freely circulating immune complexes can be very high temporarily, so that most of the "free" antibodies and antigens can be bound therein.

DETAILED DESCRIPTION OF THE DRAWINGS

DETAILED DESCRIPTION OF THE INVENTION

Figure 1:
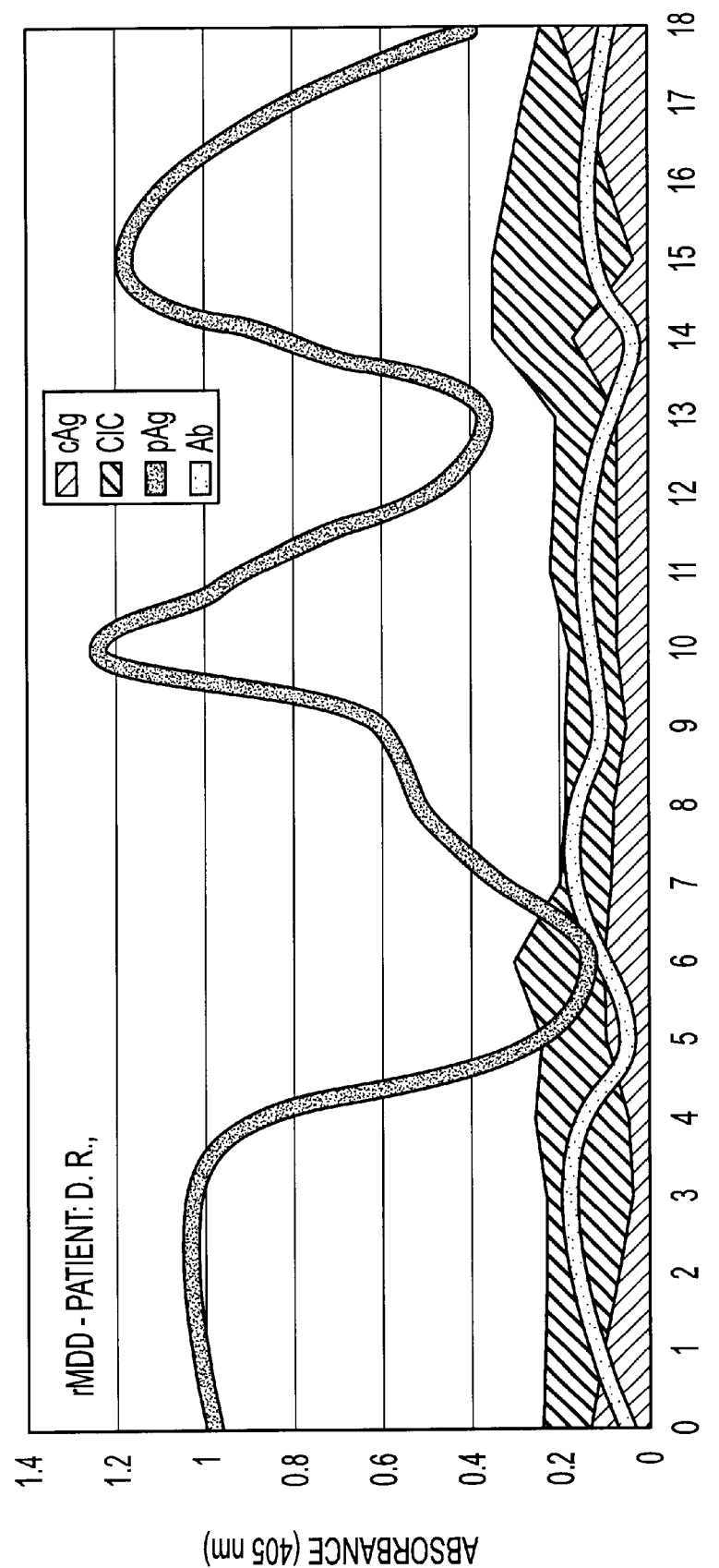
FIG. 1 shows the data of a human patient during hospitalization (treatment with antigen depressants, no antiviral treatment).

Based on the above finding, a development of the invention introduces an entirely novel diagnostic concept for the virtually complete identification of persistent BDV infections. The newly discovered parameter, CIC, is determined in combination with parameters which are already known, with antigens (AG) and antibodies (Ab), which allows the detection of various phases of the persistent BDV infection which was hitherto impossible. The antigens which are additionally determined in this context are preferably the BDV nucleoprotein p40 (relative molecular weight 40 kDa), also termed "N protein", and the BDV phosphoprotein p24 (relative molecular weight 24 kDa), also termed "P protein". The combined process provides a complete assay system in which an assay combination composed of the determination of BDV-specific circulating immune complexes (CICs) in the blood plasma, BDV-specific proteins (antigens, AG) in leukocytes (PBMCs) and in the plasma and/or BDV-specific antibodies (Ab) in the blood plasma is carried out.

The body fluid specimen to be assayed is preferably a blood specimen, it being possible for all parameters to be determined on a single blood specimen of approx. 10 ml citrated blood.

The blood specimen can be treated as follows:
(a) a blood plasma fraction is isolated from the blood specimen, and the following assays are carried out independently of one another on the blood plasma, spinal fluid or urine specimen:
  (1) an antigen detection for BDV antigens,
  (2) an antibody detection for BDV-specific antibodies,
  (3) a CIC detection;
(b) a blood plasma fraction and a leukocyte fraction are prepared from the blood specimen, and the assay in accordance with (a) (1) is carried out on the leukocyte fraction—in the case of a blood specimen—and/or on the blood plasma fraction.

By means of the invention, it was possible for the first time to demonstrate with reference to a large number of assays that the CICs play a key role in diagnostics, but also in the understanding of the course of the infection. As has been found, CICs persist considerably longer than soluble BDV antibodies which can be identified with Ab assays and longer than cell BDV AG, which is only found during the acute clinical phase. CICs can still be detected after prolonged symptom-free phases when Ab assay and AG assay are negative, and allow the conclusion that activation phases during which AG was liberated have taken place and that Ab which complex this AG have existed.

By introducing the CICs as diagnostic assay parameter which is used, if appropriate, in combination with Ab and AG, the invention closes a diagnostic gap which has previously been impossible to close.

It is known for a variety of systems that circulating immune complexes, i.e. freely mobile AG/Ab complexes, exist in principle. Free complex formation of AGs with Ab in the serum and vice versa has already been exploited for a variety of immunological assays. The existence of CICs in BDV infections, in particular the long-term high CIC concentration, even during the latent interval, and the associated diagnostic relevance of the CICs, was hitherto completely unknown.

In some patients with endogenous affective disorders and BDV infections, weekly controls even during the acute phase show that extremely high CIC concentrations, but no free Ab and no AG can be measured in PBMCs. Conventional diagnostics would miss these patients completely. With such a course of the infection, it must be assumed that the BDV-AG formed in these PBMCs in high concentrations immediately enters the plasma and is bound by the Ab present in CICs.

This is why the CIC determination described in the invention, in particular the assay combination of CIC, AG and Ab measurement, meets for the first time requirements of persistent BDV infection with its course, which varies between latency and activation, and has therefore gained great importance, not only for the diagnostic monitoring of diseased individuals, but also for identifying latent infections in healthy individuals.

In the case of high-risk patients, an obligatory CIC determination permits a BDV diagnostic which is no longer limited to the acute illness. While owing to the low viral activity the study of latent infections in healthy individuals was possible theoretically, albeit only with frequent checks, this was virtually impossible under realistic conditions. The use of the CIC assay and the assay combination allow latent infections of healthy individuals to be detected, which is of epidemiological importance since the infection sources and the transmission mechanisms remain unknown in humans and animals.

The use of the processes according to the invention is suitable for identifying BDV infections in humans and animals and possible independently of the clinical illness. The detection process according to the invention allows the quantitative measurement of BDV-specific CICs for humans and various animal species.

The term "detection" is always used in the terminology of the present invention in such a way that both a first, qualitative detection and a quantitative measurement of the relevant CIC concentrations in the form of a titer are possible.

The invention proposes as suitable immunological assay or suitable process for detecting immune complexes which circulate in body fluids a process with the following steps:

(1) fixing, via the Fc region in a suitable manner on a carrier which may have been prepared for this purpose, monoclonal or polyclonal antibodies which specifically bind to the antigens contained in the CICs;

(2) bringing into contact with the antibodies a body fluid specimen, preferably a blood plasma specimen, which is to be assayed for the presence of CICs;

(3) bringing into contact with the specimen treated in accordance with steps (1) and (2) a secondary antibody of a species other than the assayed species, preferably a goat-anti-species antibody, which is specific for antibodies of the species whose body fluid specimen was used;

(4) detection and/or measurement of the quantity of the secondary antibody by a suitable immunological detection process.

For this purpose, the antibodies used in step (1) are preferably monoclonal BDV-specific N and/or P protein antibodies which have been obtained, for example, from mice.

The support which may have been prepared in a suitable manner can be an absorptively fixing polymer assay plate or a corresponding test tube, this plate or the tube preferably first being occupied as completely as possible with secondary antibodies which are directed specifically for the species from which the CIC-antigen-specific antibodies were obtained, and, in a subsequent plate preparation step, the CIC-antigen-specific antibodies being applied to this layer of secondary antibodies.

Alternatively, fixing of the CIC-antigen-specific antibodies in step (1) of the process may also be effected with a suitable, different process, which allows the antibodies to be fixed securely on the plate in the suitable orientation, for example by applying a Clq base layer to a polystyrene support. The application of such a base layer generally permits a more economical use of the more expensive CIC-specific antibodies.

The detection in accordance with step (4) of the process can be effected, for example, via an enzyme-coupled secondary antibody at which a color reaction is triggered with a suitable substrate. In the currently preferred embodiment, the secondary antibody is coupled to alkaline phosphatase and visualized, or made measurable by means of optical detectors, with p-nitrophenyl phosphate by exploiting the reaction between the alkaline phosphatase and the paranitrophenyl phosphate, which leads to a yellow color.

A secondary antibody for the purposes of the invention is an antibody which is not specific to an antigen, but to another antibody, i.e. an antibody, of a different species, which is recognized as "foreign".

CIC determination can be effected in any body fluid which contains these CICs in sufficient concentration. In the currently preferred embodiment, the body fluid preferably used for the assay is a blood plasma specimen obtained from citrated blood. However, spinal fluid may also be used, inter alia.

BDV antigens and BDV-specific antibodies are required for the assay combination. The antigen source may be BDV-infected cells. The assay is not influenced or distorted when (homogenized) antigen-containing cell suspensions are used directly instead of isolated antigens. In an assay cited in the examples (see "Ab assay"), for example, a dilution of a 10% brain suspension of a horse which had died from Borna disease was used.

The applicant has deposited, at the Deutsche Sammlung für Mikroorganismen und Zellkulturen [German Collection of Microorganisms and Cell Cultures], fetal human oligodendroglia cells which grow as a cell line, are persistently infected with BDV, and are free from other viruses and from mycoplasmas. This deposition was done in accordance with the provisions of the Budapest Treaty on Dec. 12, 1997; the name and identification number "DSM ACC 2334" was assigned to the culture OLIGO/TL.

The cell line originates from the applicant's material. The fetal human OL cells are persistently infected with BDV, without CPE. The internal name of this cell line, which has been passaged approximately 110 times, is OLIGO/TL (or OL/TL).

Antigen which is suitable for the use in accordance with the invention can be obtained at any time from these cells. Also, other cell lines, for example also animal cell lines, can be infected with the aid of this cell line. The titer is approx. $10^3$ FFU/ml. In particular, the cells also contain the above-described antigens p40 and p24.

BDV-specific monoclonal or polyclonal antibodies can be produced at any time in a manner known per se with the aid of the cell suspension as such or else with proteins isolated therefrom. Monoclonal N and P antibodies from mice are currently preferred. To this end, mice are infected or immunized, and hybridoma cultures produced from their B cells, as usual. The supernatants are assayed (screened) for antibodies which "stain" BDV-specifically. For obtaining antibodies, see also "H. Ludwig et al., Arch. Virol. (1993) Suppl. 7:111–113".

The invention furthermore encompasses a diagnostic kit for detecting BDV infections. This kit, or this assay or detection system, comprises BDV-specific monoclonal or polyclonal antibodies, means for contacting these antibodies with a specimen suspected of containing BDV antigens or BDV CICs, and means for detecting the attached antigens or antigen/antibody complexes (CICs). Alternatively, the kit contains BDV-specific monoclonal or polyclonal antibodies occupied with BDV antigens, means for contacting these antigen-occupied antibodies with a specimen if the latter is suspected of containing BDV antibodies, and means for detecting the BDV antibodies which attached themselves in this case.

The diagnostic kit can further encompass a unit on which, or in which, the BDV-specific antibodies are present in immobilized form. Such a unit can be an assay plate which has been prepared in a particular manner, or a test tube which has been coated on the inside.

In a preferred immobilization method, the BDV-specific antibodies are monoclonal or polyclonal antibodies obtained from a species I which have been immobilized by being applied, and thus held in place, on a support, preferably in the form of an assay plate or a test tube, which has been coated with a species II-anti-species I IgG obtained from a different species (species II).

Also preferably, the antibodies of species I are polyclonal or monoclonal mouse antibodies, preferably monoclonal mouse antibodies which are specific for protein P and/or protein N, the adsorptive coating of the support being composed of an anti-mouse-IgG, preferably a goat-anti-mouse-IgG. Alternatively, the BDV-specific antibodies can also be fixed on or in the unit via polystyrene-bound Clq, or immobilized by any other suitable method.

EXAMPLES

To facilitate the understanding of the invention, the technical details of the assay combination from the treatment of the blood specimen to the evaluation are described hereinbelow. The application is illustrated by individual examples. The examples are exclusively intended for illustrative purposes. Naturally, the principles of the invention can also be realized in a different fashion.

Part I: Processing of the Specimen Material to be Assayed 10 ml of citrated blood are required for the test for BDV infection. 9 ml of venous volunteer blood are added to 1 ml of an 0.106-molar sodium citrate 2-hydrate solution and the specimen is mixed thoroughly. It is recommended to use ready-to-use citrate tubes, for example the 10 ml Monovette 9NC by Sarstedt. Until the specimen is sent to the test laboratory, it should be stored at 4° C. The specimen quality is not adversely effected when posted by express delivery without refrigeration (1 to not more than 3 days).

The citrated-blood specimen is separated using density-gradient centrifugation into the plasma fraction and the cellular blood components. The plasma fraction is used to assay for CIC, AG and Ab. The cell fraction of the leukocytes (PBMCs) is processed and then used for AG assaying. If the intention is only to assay for CICs, or if only plasma assays are carried out, the cell fraction can be discarded.

To separate the components, Ficoll separating solutions (Biochrom) of different densities are used, depending on the animal species.

The following are required for 6 ml of blood:

Humans 3 ml Ficoll, density 1.077

Horses 3 ml Ficoll, density 1.090

Cattle 2 ml Ficoll, density 1.077+1 ml Ficoll, density 1.068

Cats 2.8 ml Ficoll, density 1.077+0.2 ml PBS pH 7.2

Dogs 2.8 ml Ficoll, density 1.077+0.2 ml PBS pH 7.2

Rabbits 2.8 ml Ficoll, density 1.077+0.2 ml PBS ph 7.2

I. Protocol for Separating a 10 ml Citrated-blood Specimen (1) Fill conical 10 ml disposable tubes with 3 ml Ficoll separating solution of the relevant density and superimpose a layer of not more than 6 ml citrated blood (2) Centrifuge specimen for 20 minutes at 1049 g (2200 rpm, Heraeus Christ Minifuge) (in the case of all specimens with Ficoll of density <1.090); in the case of Ficoll of density of 1.090, centrifuge for 20 minutes at 1249 g (2400 rpm)

(3) Carefully remove plasma fraction (supernatant), using disposable Pasteur pipette; for immediate assaying the same day, store at 4° C.; for later assaying, store at −20° C.

(4) The leukocyte fraction forms a discernible ring on or above the Ficoll, while the erythrocyte fraction (not required) is present in the Ficoll as a pellet. After removal of the plasma, remove cell ring using disposable Pasteur pipette and transfer into a fresh conical 10 ml plastic tube, make up with PBS and mix thoroughly (5) Centrifuge leukocytes (PBMCs) for 10 minutes at 1952 g (3000 rpm). Discard supernatant and take up pellet in not more than 0.5 ml PBS=approx. 10-fold concentration. Transfer solution into sterile freezer tubes (for example Nunc, 1.5 ml) equipped with screw top.

(6) For immediate assaying of internal BDV antigens (see below), store the cells in PBS at 4° C.; for assaying at a later time, store at least at −20° C., better at −70° C.

II. Assay Systems

An assay combination of EIA (enzyme immunoassay)—basis (solid-phase assay) is used for assaying AG in PBMCs and/or in blood plasma and CIC and Ab in plasma. The first two assay steps are the same for all three assay systems. The subsequent description in the form of assay protocols is therefore divided into (A) coating of the assay plates (A1) and (A2) and (B, C, D) protocol for the AG, CIC and Ab assay.

EIA Protocol (Double-sandwich Type)

(A) Protocol for Coating the EIA Plates

Maxi Sorp immunomodules (Nunc® Maxi Sorp F8, Cat. No. 469949) were used as polymer supports for the subsequent reactions. One frame accommodates 12 modules with 8 vertically arranged shallow polymer recesses and have exactly the dimensions of a 96-well microtiter plate (standard dimension for EIA systems):

(A1) 0.1 ml per well AffiniPure® goat-anti-mouse IgG, Fc fragment, absorbs against human, bovine, equine serum proteins (Dianova® Cat. No. 115-005-071), diluted 1:1000 (=1.8 micrograms protein per milliliter) in coupling buffer; incubation overnight at 4° C. or for 2 hours at 37°.

Wash 3× in wash buffer (Dynatech 96-well plate washer)

(A2) 0.1 ml per well monoclonal antibodies against the BDV N-protein p40 and BDV P-protein p24 (W1 and KFU2, ref.: Arch. Virol. (1993) Suppl. 7:111–133) (as catch antibodies), in each case diluted 1:500 in dilution buffer. Incubation for 2 hours at 37° C. or overnight at 4° C.

The plates can then be stored at 4° C. up to at least 4 weeks before being used further.

(B) Protocol for the Determination of BDV Antigens (AG) in PBMCs

Preparation

Wash the A2-coated plates 3× in wash buffer

Ultrasonic treatment (20 cycles $min^{-1}$, 40 mA) (Branson Sonifier B15P; ref. Mol. Psychiatry (1996) 1:200–212) of the PBMCs isolated in I.

AG Assay (B1) Specimen dilution: into each well of the precoated plates introduce 0.1 ml dilution buffer, add in A sonified PBMCs (0.1 ml) or blood plasma (0.1 ml) (=1:2) and continue diluting a further 7 steps to basis 2 (to 1:256); incubate overnight at 4° C.

Wash 3× in wash buffer (B2) per well 0.1 ml BDV-specific rabbit antiserum (for example GC 12, immunofluorescence titer 1:1000) (=detection antibody) in suitable dilution (1:1000, 10-fold more concentrated than the IF titer) in dilution buffer; incubate for 2 hours at 37° C.

Wash 3× in wash buffer (B3) per well 0.1 ml alkaline-phosphatase-coupled Affini Pure® goat-anti-rabbit IgG, Fc-fragment-specific, absorbs against human serum proteins (Dianova®, Cat. No. 111-055-046) (=secondary antibody), diluted 1:3000 in conjugate dilution buffer; incubate for 1 hour at 37° C.

Wash 3x in wash buffer (B4) per well 0.1 ml of the substrate solution (1 mg/ml p-nitrophenyl phosphate; Sigma, obtainable as substrate tablets) in substrate dilution buffer; incubate for 5–10 minutes at room temperature or until the color reaction develops (color change from colorless to yellow) in the positive control.

(B5) per well, add 0.05 ml of stop solution (3-molar NaOH solution)

(B6) Measure at 405 nm in a microtiter plate Multiscan (for example BIO RAD 2550 EIA READER or Dynatech); blank measurement against unreacted substrate. Semiquantitative evaluation sufficient: (+)=weekly positive, to a maximum of 4+=extremely positive; +/−means inconclusive and requires a second test. (Example see under Use).

(C) Protocol for the Determination of BDV-specific Circulating Immune Complexes (CICs) in the Blood Plasma Preparation Wash the A2-coated plates 3x in wash buffer CIC Assay (C1) Specimen dilution: into each well of the precoated plates, introduce 0.1 ml dilution buffer; in A: add 0.09 ml dilution buffer+0.01 ml of the blood plasma prepared under I. (=dilution 1:20), continue diluting a further 7 steps to basis 2 (to 1:2560); incubate for 1–2 hours at 37° C. (standard time: 1 hour at 37° C.).

Wash 3x in wash buffer (C2) per well 0.1 ml alkaline-phosphatase-coupled goat-anti-species (corresponding to the species of the specimen) IgG, Fc fragment (also obtainable from Dianova®) (=secondary antibody), dilution 1:3000 in conjugate dilution buffer; incubation for 1 hour at 37° C.

Wash 3x in wash buffer (C3) per well 0.1 ml of the substrate solution (1 mg/ml p-nitrophenyl phosphate; Sigma, obtainable as substrate tablets) in substrate dilution buffer; incubate for 5–10 minutes at room temperature or until the color reaction develops (color change from colorless to yellow) in the positive control.

(C4) per well, add 0.05 ml of the stop solution (3-molar NaOH solution).

(C5) Measure at 405 nm in a microtiter plate Multiscan (for example BIO RAD or Dynatech); blank measurement against unreacted substrate. Semiquantitative evaluation from (+) to 4+ sufficient (cf. also Assay B); however, titer indications with end-point determination also possible. (Examples see Use).

(D) Protocol for the Determination of BDV-specific Antibodies (Ab) in the Blood Plasma Preparation Wash the plates coated up to A2 3x in wash buffer Ab Assay (D1) per well 0.1 ml of a 10% brain suspension (=detection antigen) of a horse which has died from Borna disease, in a suitable dilution (1:50) in dilution buffer; alternatively, use can be made of cell culture supernatant of the cell line deposited on 12.12.1997 under No. DSM ACC2334 at the DSMZ which is persistently infected with a Borna disease viral strain, diluted between 1:100 and 1:300 in dilution buffer,

[lacuna] of blood plasma, prediluted 1:5 (=dilution 1:50), predilute a further 7 steps to basis 2 (to 1:6400); incubate for 1 hour at 37° C.

Wash 3x with wash buffer (D3) per well 0.1 ml of alkaline-phosphatase-coupled goat-anti-species (corresponding to the species of the specimen) IgG, Fc-fragment-specific (Dianova®) (=secondary antibody), diluted 1:3000 in conjugate dilution buffer; incubate for 1 hour at 37° C.

Wash 3x in wash buffer (D4) per well 0.1 ml of the substrate solution (1 mg/ml p-nitrophenyl phosphate; Sigma, obtainable as substrate tablets) in substrate dilution buffer; incubate for 5–10 minutes at room temperature or until the color reaction develops (color change from colorless to yellow) in the positive control.

(D5) per well, add 0.05 ml of the stop solution (3-molar NaOH solution).

(D6) Measure at 405 nm in a microtiter plate Multiscan (for example BIO RAD or Dynatech); blank measurement against unreacted substrate. Evaluation possibilities as in Assay C.

III. Buffer Solutions

Coupling Buffer

Stock solution A: 0.02 M $NaH_2PO_4.H_2O$ 2.76 g; dd—water to 1000 ml

Stock solution B: 0.02 M $Na_2HPO_4.2H_2O$ 3.561 g; dd—water to 1000 ml

Working Solution 65 ml solution A+45 ml solution B+14.6 g NaCl, dd—water to 1000 ml, pH 7.6.

| Wash buffer: | | |
|---|---|---|
| NaCl | 45 g | (9 g per 1000 ml) |
| Tween 20 | 2.5 g | (0.5 g per 1000 ml) |
| $NaN_3$ | 1.0 g | (0.1 g per 1000 ml) |
| dd - water to 5000 ml | | |

| Dilution buffer: | |
|---|---|
| $KH_2PO_4$ | 0.2 g |
| $Na_2HPO_4 \cdot 12H_2O$ | 2.9 g |
| NaCl | 8.0 g |
| KCl | 0.2 g |
| Tween 20 | 0.5 g |
| $NaN_3$ | 0.2 g |
| dd - water to 1000 ml, pH 7.2 must be checked or established. | |

| Conjugate dilution buffer (TBS-TWEEN): | |
|---|---|
| Dissolve in 900 ml dd - water | |
| TRIS | 2.4 g |
| NaCl | 8.0 g |
| KCl | 0.2 g |
| Tween 20 | 0.5 g, | bring to pH 8.0 with concentrated HCL, then make up to 1000 ml.

| Substrate dilution buffer (DIETHANOLAMINE BUFFER): | |
|---|---|
| Dissolve in 843 ml dd - water | |
| diethanolamine | 97 ml |

| Substrate dilution buffer (DIETHANOLAMINE BUFFER): | |
| --- | --- |
| MgCl$_2$ | 0.1 g |
| NaN$_3$ | 0.2 g, |
| then add 60 ml 1 N HCL, bring to pH 9.8. | |

| Stop solution (3 M NaOH): | |
| --- | --- |
| NaOH | 120 g |
| dd - water to 1000 ml | |

IV. Sources of Commercially Available Reagents for the Assay Systems Described
1. Ficoll separating media: Biochrom KG, D-12247 Berlin
2. Citrate tubes: Sarstedt, D-51588 Nümbrecht
3. EIA microtiter strips (Maxi Sorp immunomodule) F-form: Nunc, Roskilde, Denmark
4. Enzyme conjugates for secondary antibodies: Dianova, manufacturer: Jackson Immuno Research Labs Inc., West Grove, Pa., USA
5. Washer for EIA assays: Dynatech Ultrawash plus; Dynatech Labs. Inc. Chantilly, Va., USA
6. Substrate for enzyme conjugates (for alkaline phosphatase): Sigma Chemical Co., St. Louis, Mo., USA
7. Buffer substances (in III) with the exception of KCL: Merck KGaA, D-64271 Darmstadt, Fluka Chemie AG, CH-9471 Buchs
8. Photometer (for microtiter plates): BIO RAD Labs. Hercules, Calif., USA or Dynatech Labs Ind., Chantilly, Va., USA
9. Sonifier for cell disruption of the PBMCs: Branson Sonifier, B15JP, Branson Sonic Power Company, Danbury, Conn., USA V. BDV-specific Reagents 1. Monoclonal Antibodies: Needed as Base Coating (Step A2) for Assays B, C, D 1a) W1, recognizes a sequential epitope on the N-protein (p40) of BDV. The binding site is conserved, i.e. is recognized by more than only the host species. The antibody is characterized in the reference Arch. Virol. (Suppl.) (1993) 7:111–133.

1b) KFU 2, recognizes a sequential epitope on the P-protein (p24) of BDV. The binding site is conserved, i.e. is recognized by more than only the host species. The antibody is characterized in the reference Arch. Virol. (Suppl.) 7:111–133 (1993).

2. Rabbit Antisera (Specific Detection Antibodies): Required for Assay B (AG) in Step B2

It is possible to use the sera of experimentally infected rabbits (reference as under V, 1a). They must have a minimum titer of 1:2000 in the immunofluorescence assay and recognize at least the N- and P-proteins of BDV (p40 and p24) in the Western blot. Since Borna viruses are genetically highly stable according to present knowledge, i.e. the sequences in different viral strains show only minor differences, polyclonal antisera generally recognize the proteins of Borna viruses from different species.

This also applies to the few human strains which have been obtained to date (reference Mol. Psychiatry (1996) 1:200–212; Virus Res. (1996) 44:33–44.), even though the human strains show relevant point mutations at amino acid level which have not been found as yet in animal strains.

In addition to the serum GC12 which has been mentioned in the description of the assay and other antisera obtained by infection with the animal reference strain V, it is possible to use defined rabbit sera which have been generated by experimental infection with the different human BDV strains (reference Mol. Psychiatry (1996) 1:200–212) and which recognize the entire spectrum of viral proteins.

3. Defined Antigen Suspensions Required for Assay D (Ab Assay) in Step D

Brain suspensions (10%) of horses which have died from Borna disease contain a high concentration of viral proteins (in particular N- and P-proteins). A progressive neurological disease which develops as a consequence of BDV infection and ends in death is rare compared with periodically occurring, spontaneously remittent behavioral disorders or BDV infections with a subclinical course (reference: Arch. Virol (1997) Suppl. 13:167–182). The encephalitis which is termed the so-called classic Borna disease is probably caused by a virus production which has gone out of control. The virus titers in the brain reach $10^5$ to $10^6$ FFU/ml and are thus within the range of experimentally infected laboratory animals (reference: Prog. med. Virol. (1988) 35:107–151).

Antigen suspensions which can be employed are directly defined brain suspensions whose virus and antigen titers have been determined. Suspensions from cell lines which are persistently infected with BDV (human and animal strains) can also be used for the Ab assay as described. These persistently BDV-infected cell lines are particularly suitable for standardization purposes. Cell lines which can be used are deposited at the DSMZ in accordance with the provisions of the Budapest Treaty under number DSM ACC 2334 (date of deposition Dec. 12, 1997).

Defined antigen solutions can be employed as positive control in assay B (AG assay).

VI. Brief Description of the Test Principles of the Assay Combination Described in the Invention The assay combination is designed as a triple assay for three different BDV test parameters which are relevant for the infection, viz. Antigen (AG, assay B), circulating immune complexes (CIC, assay C) and antibodies (Ab, assay D) in a single blood specimen. The assays can also be carried out individually, for example for testing very specific putative phases of the disease. The assays are designed as solid-phase assays and are evaluated photometrically. Assay reactions and procedures take place in microtiter systems, which are modern laboratory standards.

Part A, which is used as base coating, is exploited equally by all three, or four, assays. The base coating is a core piece of the assay combination and is responsible for the high BDV specificity. The latter is generated by a set composed of two monoclonal antibodies which are directed against conserved epitopes of the N- and P-proteins of Borna virus (p40, p24). A very efficient use of these catch antibodies is achieved by a precoating with an anti-mouse antibody. Without this precoating, it is necessary to subject the specific monoclonal antibodies to purification by affinity chromatography. In assay B for the AG detection, p40 and p24 proteins which are (freely) present in the blood plasma or in the PBMCs are bound by the catch antibodies. Polyclonal rabbit detection antibodies, which are also BDV-specific, recognize the bound antigen from the specimen and it is visualized by the enzyme-coupled indicator system. This double-sandwich principle has the advantage that small amounts of BDV antigen become detectable in a large quantity of cell proteins owing to the specific binding to two different antibody systems.

In assay C for the CIC detection, the antigen moiety of BDV immune complexes present in the plasma is bound by the catch antibodies. In the next reaction step, the antibody moiety of the immune complex is bound by an enzyme-labeled anti-antibody (secondary antibody), and this binding is visualized via the indicator system. This assay design, which is amazingly simple under realistic conditions, visualizes only those CICs which are BDV-specific and thus diagnostically relevant. This assay is the core of the invention and closes the diagnostic gap which has existed to date. BDV-specific CICs were discovered by the inventors, and their detection was developed.

In test D for the Ab detection, BDV antibodies to p40 and p24 which are (freely) present in the plasma are determined via a detection antigen solution which has previously been bound by the catch antibodies. The specifically bound antibodies are visualized via enzyme-labeled anti-antibodies (secondary antibodies), the indicator system. The assay design has the advantage that unpurified infected brain or cell culture suspensions can be used as detection antigen solution without a loss in specificity. The specificity is guaranteed by the catch antibodies.

A purified antigen solution will always be required for other, more simple EIA-based Ab assays, and this purified antigen solution must be bound to the polymer support as a solid phase. While these assays are more rapid to carry out, antigen purification means that they are complicated and expensive.

The standard BDV antibody assay currently carried out in other institutions is the indirect immunofluorescence assay (reference: J. Med. Virol. (1992) 36:309–315). The assay has the advantage over new systems in that the results can be compared quantitatively and qualitatively with those from other laboratories (Review: CTMI (1995) 190:103–130). Immunofluorescence titers are generally lower than EIA titers. In the longitudinal-section studies shown in Section VII, the antibodies were detected by immunofluorescence to ensure that they can be compared with other laboratories'results obtained on a merely serological basis.

The EIA-based Ab assay shown in the assay combination improves the detectability of the antibodies owing to its higher sensitivity, but ultimately changes nothing regarding the drop below the detection limit and below titers described in the introduction. This is why a lack of Ab detection with conventional methods does not exclude BDV infection. The occurrence of free antibodies, which is only a temporary phenomenon, can be explained by the formation of CICs.

The four assay parameters define the following diagnostic principle:

cAG: The antigen assay from PBMCs is suitable as acute marker for virus replication. cAG can only be measured briefly during the disease phase.

pAG: The antigen expressed into the plasma is the result of virus replication in the cells. It generally appears somewhat later than cAG, but sometimes also simultaneously, and can frequently be detected over several weeks. pAG is also an acute marker during the disease phase. However, its detectability depends on the rate at which the antibodies and subsequently the CICs are formed. Course studies (weekly) have found that only pAG is measured positively in some specimens (for example week 1; only pAG, week 2: pAG+ CIC etc.).

CIC: The circulating immune complexes are very good infection markers and therapy control markers. With antiviral therapy, disappearance of the CICs, or no neogenesis, are observed over a prolonged period. The half-life of the CICs is four weeks in theory; however, CICs can frequently still be detected many weeks after the acute pathological process. No therapy means that an alternating CIC level is generally retained. CIC measurement is therefore also suitable for healthy individuals as screening for latent infections.

Ab: Antibodies only occur when stimulated by the antigens. During the acute phase, the antibody titer is low or not detectable since the antibodies are bound in the immune complexes. The antibodies can be detected better during convalescence. (Note: it must be noted that the data published earlier by third parties always refer to the immunofluorescence assay (IF), which is considerably less sensitive, so that antibodies could only be detected occasionally.

In the use examples which follow, it is demonstrated that the stage of the infection changes constantly (especially during the disease phase) and that the detection of a plurality of parameters is ideal diagnostically for this type of a persistent virus infection (with a low replication rate during the activation phases).

VII. Use Examples of the Invention

Three case examples from the human sector and two case examples from the animal sector are described in the following text. These examples were selected from a large number since it was possible to study an above-average specimen size (up to 23 from one individual) over especially long observation times of up to 7 months.

Human Patient 1: (Initials D. R.)
  Sex: Male
  Age: 59 years
  Clinical diagnosis: recurrent endogenous depression (rMDD-recurrent major depressive disorder), plus neurotic aspects
  Examination: during the acute depressive episode
  Observation time: 27 weeks (approx. 7 months, May–November 1996)
  Number of specimens: 23, of which 13 at 1-week intervals
  Summary of the assay result:
    Antigen: 4/23
    CIC: 23/23
    Antibodies: 0/23

Human Patient 2: (Initials G. R.)
  Sex: Female
  Age: 76 years
  Clinical diagnosis: rMDD
  Examination: during the acute depressive phase
  Observation time: 21 weeks (approx. 5 months, June to November 1996)
  Number of specimens: 18 (of which 14 in 1-week intervals)
  Summary of the assay result:
    Antigen: 4/18
    CIC: 17/18
    Antibodies: 3/18

Human Patient 3: (Initials A. J.)
  Sex: Male
  Age: 63 years
  Clinical diagnosis: rMDD
  Examination: during the acute depressive episode
  Observation time: 6 weeks (August to September 1996)

Number of specimens: 7, all at 1-week intervals
Summary of the result:
    Antigen: 1/7
    CIC: 4/7 (2 specimens +/−)
    Antibodies: 1/7
Equine Patient 1: (A. S., from North-Rhine Westphalia)
    Sex: Male, gelding, Hannoverian
    Age: 11 years
    Clinical diagnosis: Borna disease, severe episode of apathy, somnolence, loss of appetite, altered feeding behavior; spontaneous remission (Arch Virol (1993) Suppl 13, in press)
    Examination: during the acute disease phase and after convalescence Start: 3 weeks after the beginning of the illness)
    Observation time: 28 weeks (7 months, June 1995 to January 1996)
    Number of specimens: 8 (6 complete examinations)
    Summary of the assay result:
        Antigen: 4/6
        CIC: 4/6
        Antibodies: 5/6
Equine Patient 2: (F. D.) from Bavaria
    Sex: Male, Bavarian gelding
    Age: 15 years
    Clinical diagnosis: Borna disease, severe neurological form, euthanasia (August 1996); first episode in 1994, with spontaneous remission
    Observation time: 14 weeks (May to August 1996)
    Number of specimens: 3 blood specimens, 1 spinal fluid specimen
    Summary of the assay result:
        Blood:
            Antigen: 2/3
            CIC: 3/3
            Antibodies: 0/3
        Spinal fluid:
            Antigen: Finding +/0
            CIC: 1/1
            Antibodies: 0/1

The age distribution of the human patients in the case examples selected is atypical. There are similar courses from all age groups. The courses are typical for affective diseases with recurrence (either rMDD or bipolar illness), examined during the acute disease phase.

During the symptom-free interval, low CIC concentrations usually remain, while antigen in PBMCs and antibodies are no longer detectable. The duration of CIC persistence, and the titer level, depend on the intensity of the previous activation phase of the BDV infection. According to the examinations which we have carried out so far, the CICs persist for at least 3 months (after the disease episode). No systemic data exist for very long symptom-free intervals (for example several years). We know from individual examinations that even the CICs can disappear. When a new depressive episode starts after a long healthy interval, the status during the initial examination can be negative for all 3 parameters. To guarantee that BDV infection can be excluded, a single examination is therefore not sufficient. Rather, at least one second examination during the first third of the disease episode is necessary. If infection is present, then at least CICs are found, as a rule, while the AG or Ab findings are still negative.

Under realistic conditions, this means that, taking into consideration a time interval, BDV infection can be detected sufficiently reliably by the CICs shown in the invention and by the novel triple test which also takes into consideration AG and Ab.

The case examples of the equine patients deal with diseased, infected animals. Healthy, symptom-free carriers of the infection can frequently only be detected by CICs. Examples of examinations in healthy groups are shown under X.

Comment

Human patient 1 is a specific case since he belongs to the small number of patients where almost exclusively exorbitantly high CIC concentrations, but no free antibodies and only rarely AG in PBMCs were detectable in weekly checks during the acute disease phase (see also introductory section). We assume that the BDV-AG formed in the PBMCs immediately enters the plasma and is bound in CICs by the antibodies which are present. Conventional assay methods which do not take into consideration the CICs would virtually not identify patients of this type.

Possibilities of Evaluating AG and CIC assays

As a rule, a semiquantitative evaluation which indicates the relative concentration of the parameters is preferable to a titer value. Each parameter is measured in an 8-step dilution series per specimen. The absorption, which drops in parallel with the dilution, provides an additional reliability when assessing the titer. It can be used for an end-point titer determination, but does not need to be.

VIII. Using the Assay Combination for Assessing the Actual State of the BDV Infection The AG detection in PBMCs (and in the blood plasma) is a parameter for an acute activation process. The CIC parameter assesses the past interval during course studies. When CIC values rise within the interval, this means that viral antigen has been formed and already exists in complexed form at the time of assaying. Whether free antibodies are detectable is determined by the antibody production in relation to the antigen production. If antibody production has only just restarted owing to an activation episode, free antibodies will hardly be detectable, but CICs will. At a later point in time, when antigen production is down, the chance of detecting free antibodies increases (with or without simultaneous CIC detection).

An interpretation of the triple test which takes into consideration these circumstances is very helpful for assessing clinical progresses.

The following assay constellations are possible, according to the present-day art:

1. AG-negative CIC-negative Ab-positive
    Infection is present, but has not been activated, neither acutely nor during the last weeks.
2. AG-positive CIC-negative Ab-negative
    Infection is highly acutely activated at the time of examination, but not before.
[Lacuna]
    Infection is present, activation started a few weeks ago, but activation is still acute at the time of examination.
4. AG-negative CIC-positive Ab-negative or -positive
    Infection is present, but activation began a few weeks, possibly months ago (depending on the examination interval). Activation no longer present at the time of examination.
    If this is an initial examination, only the statement "infection is present" can be made.
5. AG-negative CIC-negative Ab-negative
    No suggestion that BDV infection is present. If two assays are fully negative during the acute disease phase, infection can be excluded.

To monitor the therapy before terminating an antiviral treatment, at least two assays (interval 4–6 weeks) must be completely negative (Lancet (1997) 349:178–179).

Earlier studies have shown that CICs are a highly sensitive marker for assessing the success of antiviral therapy. They can frequently still be detected as the last parameter after clinical remissions have already taken place, but disappear later when the therapy is continued.

IX. Detection of Infection in Symptom-free Horse Populations, Deleted

The invention allows for the first time the various phases of a BDV infection to be identified (virtually) completely in more than one species by combining the newly-discovered assay parameter "circulating immune complexes", (CICs) in the blood plasma, with parameters which are already known, viz. antigen (AG) in leukocytes and antibodies (Ab) in the plasma. All three parameters can be determined on a single blood specimen. The detection, which is described for the first time in the invention, of BDV-specific CICs as the only long-term persistent infection markers allows not only healthy carriers (latent infections) to be identified, but also the course of the infection and the success of the therapy to be assessed in the case of diseased individuals. Immune complexes circulating freely in the body fluid and composed of BDV antigens and specific antibodies attached thereto are detected in a body fluid specimen to be assayed by means of a suitable immunological assay.

In the following text, a few further examples are described with reference to figures.

FIGS. 1, 2, 4 and 5 show schematically how the state of the infection (in particular during the disease phase) changes constantly, and that, diagnostically speaking, the measurement of several parameters is optimal for this type of persistent viral infection (with low replication rate during the activation phases). The data plotted are in each case the absorbance at 405 nm vs. "weeks" (course of the study). The figures show the course for CICs—circulating immune complexes cAg—cellular antigen pAg—plasma antigen Ab—antibodies (EIA)

FIG. 1 shows the data of human patient 1 (initials D. R.), a 59-year-old rMDD-patient during hospitalization (treatment with antigen depressants, no antiviral treatment). The examination period was approximately 3 months (18 weeks). Assay system: EIA; dilution: cAG 1:2, CIC 1:20, pAG 1:2, Ab 1:100; cut-off limit 0.1 specimen origin: for cAG: for cAG sonified PBMCs, otherwise suitable plasma specimens.

Figure 2:
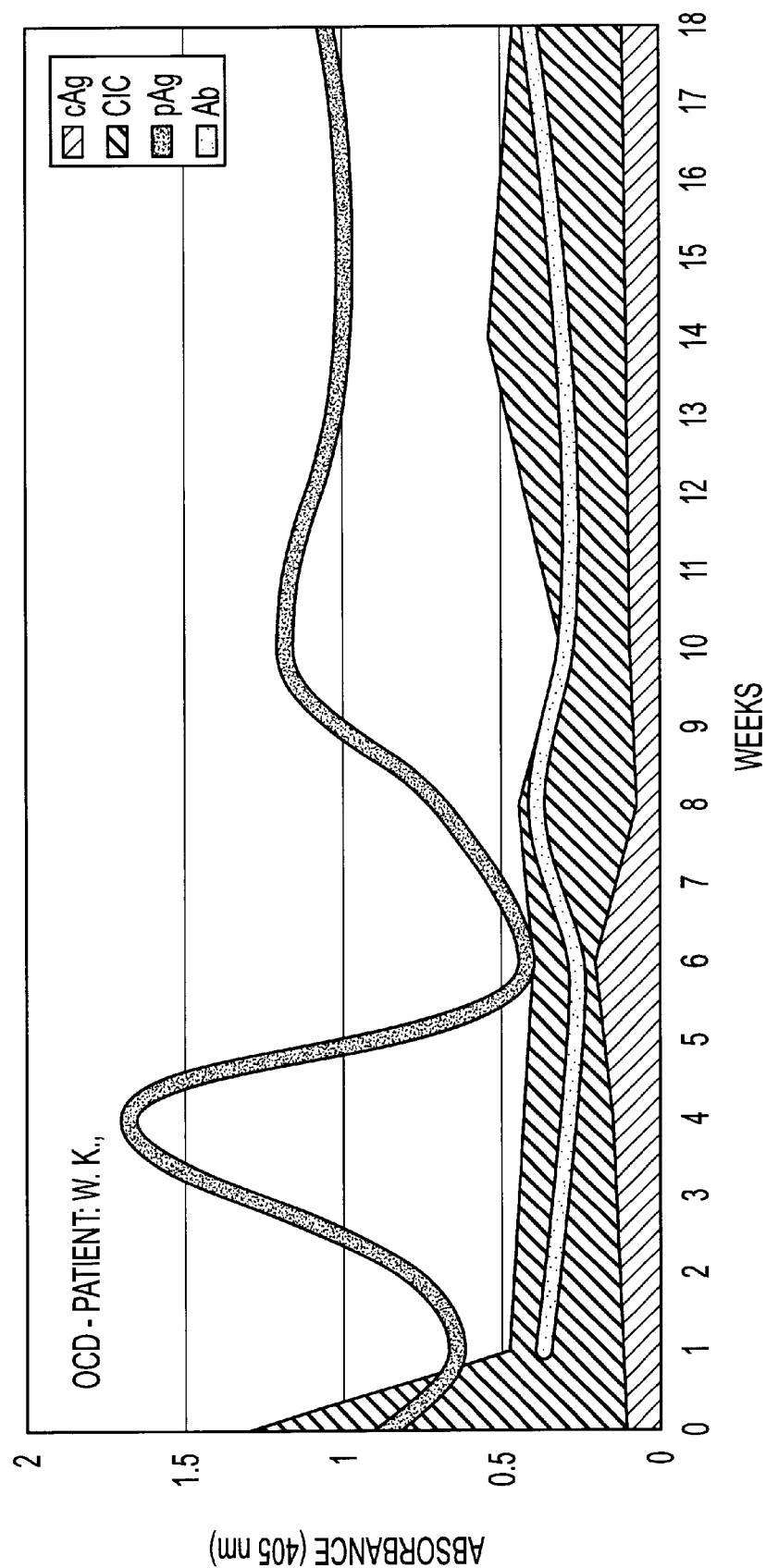
FIG. 2 shows a diagram for a 30-year old OCD patient (OCD=obsessive compulsive disorder) during hospitalization, the diagram corresponding to FIG. 1.

FIG. 2 shows a diagram for a 30-year-old OCD patient (OCD=obsessive compulsive disorder) during hospitalization, the diagram corresponding to FIG. 1. BDV infection plays a not inconsiderable role in these patients, like in the case of depressive patients. In both patient groups—viz. depressive and OCD patients—it is possible that serotonin-controlled processes are dysfunctional. The reason for this might be that the BDV virus functionally attacks certain loci in the brain and on the ganglia. FIGS. 1 and 2 show parameter developments which are similar to each other.

Figure 3:
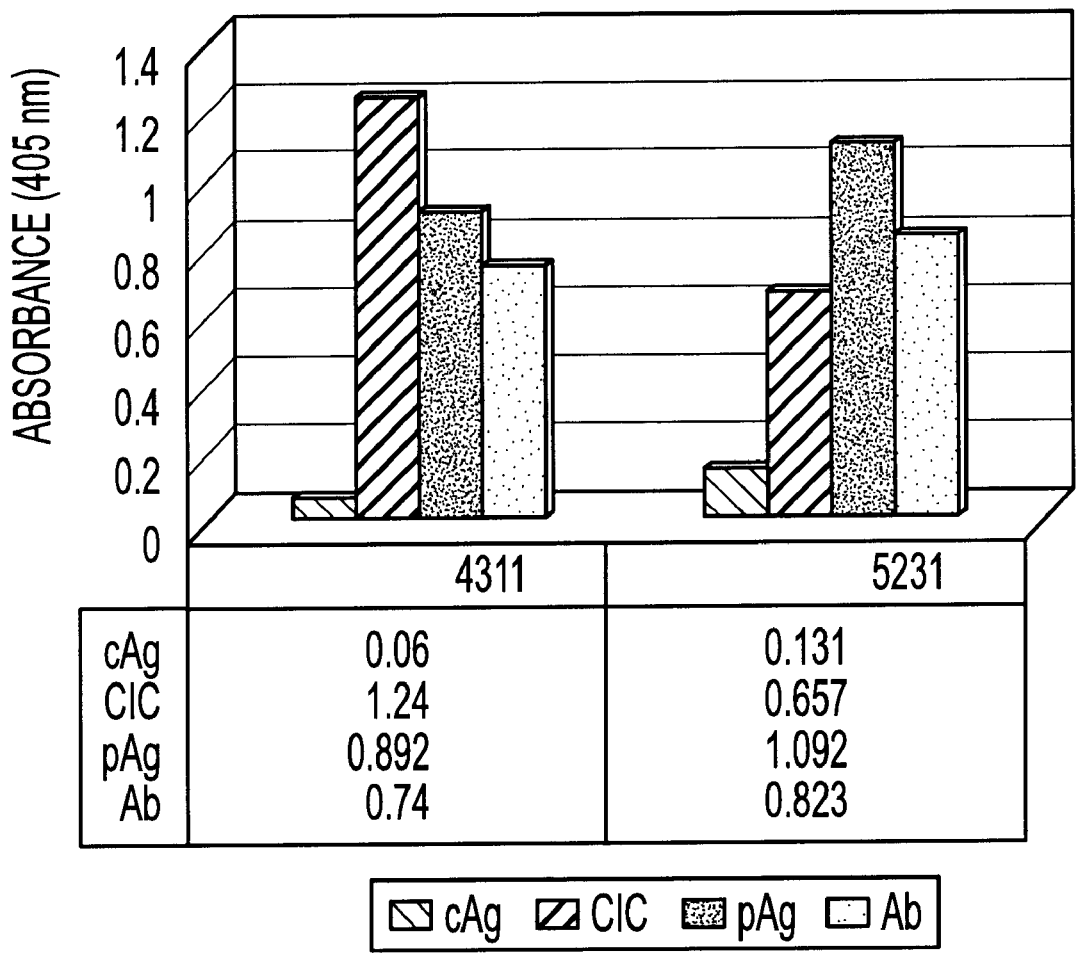
FIG. 3 shows 2 examples from the animal sector, viz. two horses suffering from Borna disease.

FIG. 3 shows 2 examples from the animal sector, viz. two horses suffering from Borna disease. In these cases, only one specimen was examined. The ratio of CIC to pAG (free plasma antigen) and Ab (=free plasma antibody (Ab), measured by EIA) can be seen clearly. Specimen 4311 was obtained from a horse from Northern Germany (initial G.) which had been examined in March 1997 owing to the (questionable) clinical diagnosis "Borna disease. The IF antibody titer was 1:40. Specimen 5231 was obtained from a horse from Southern Germany (initial D.) which had been examined in May 1997 owing to the clinical diagnosis Borna disease. The IF antibody assay was negative. The horse had fallen ill two months earlier, in March 1997, and showed apathy and somnolence. The symptoms that remained in May were head shaking and stiff gait (EIA parameters: dilution cAG 1:2, CIC 1:20, pAG 1:2, Ab 1:100, cut-off limit=0.1, base for the specimens: cAg: sonified PBMCs, otherwise suitable plasma specimens).

The data on which the figures are based are shown in tabulated form hereinbelow:

TABLE 1

(for FIG. 1):

| Absorbance (405 nm) at | cAG | CIC | pAG | Ab |
| --- | --- | --- | --- | --- |
| 0 W | 0.14 | 0.982 | 0.237 | 0.051 |
| 3 | 0.041 | 1.019 | 0.225 | 0.177 |
| 4 | 0.051 | 0.858 | 0.251 | 0.146 |
| 5 | 0.089 | 0.241 | 0.237 | 0.048 |
| 6 | 0.096 | 0.120 | 0.299 | 0.104 |
| 7 | 0.088 | 0.323 | 0.209 | 0.163 |
| 8 | 0.081 | 0.503 | 0.185 | 0.158 |
| 9 | 0.056 | 0.582 | 0.192 | 0.11 |
| 10 | 0.068 | 1.237 | 0.18 | 0.125 |
| 11 | 0.075 | 0.91 | 0.217 | 0.148 |
| 13 | 0.079 | 0.366 | 0.208 | 0.097 |
| 14 | 0.178 | 0.79 | 0.35 | 0.041 |
| 15 | 0.041 | 1.179 | 0.353 | 0.126 |
| 18 | 0.028 | 0.397 | 0.254 | 0.108 |

TABLE 2

(for FIG. 2):

| Absorbance (405 nm) at | cAG | CIC | pAG | Ab |
| --- | --- | --- | --- | --- |
| 0 W | 0.108 | 0.869 | 1.335 | |
| 1 | 0.117 | 0.639 | 0.478 | 0.367 |
| 4 | 0.146 | 1.679 | 0.438 | 0.28 |
| 6 | 0.208 | 0.421 | 0.401 | 0.263 |
| 8 | 0.08 | 0.675 | 0.439 | 0.386 |
| 10 | 0.105 | 1.174 | 0.307 | 0.296 |
| 12 | 0.096 | | | |
| 14 | | 1.009 | 0.542 | 0.307 |
| 18 | 0.134 | 1.048 | 0.474 | 0.417 |

TABLE 3

(for FIG. 3):

| | Specimen 4311 (absorbance) | Specimen 5231 (absorbance) |
| --- | --- | --- |
| cAG | 0.06 | 0.131 |
| CIC | 1.24 | 0.657 |
| pAG | 0.892 | 1.092 |
| Ab | 0.74 | 0.823 |

Figure 4A:
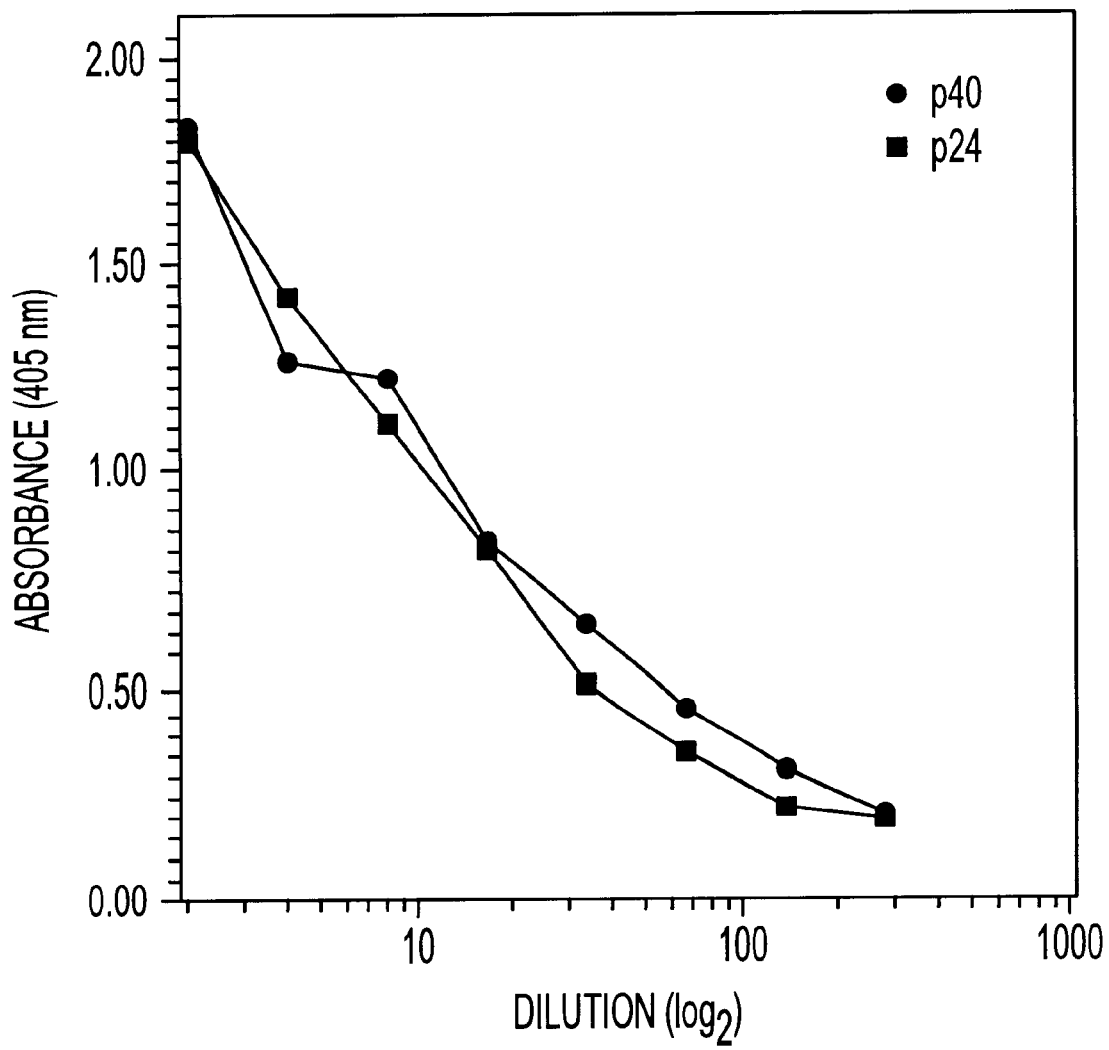
FIG. 4a shows a CSF specimen from a patient with major depressive disorder.
Figure 4B:
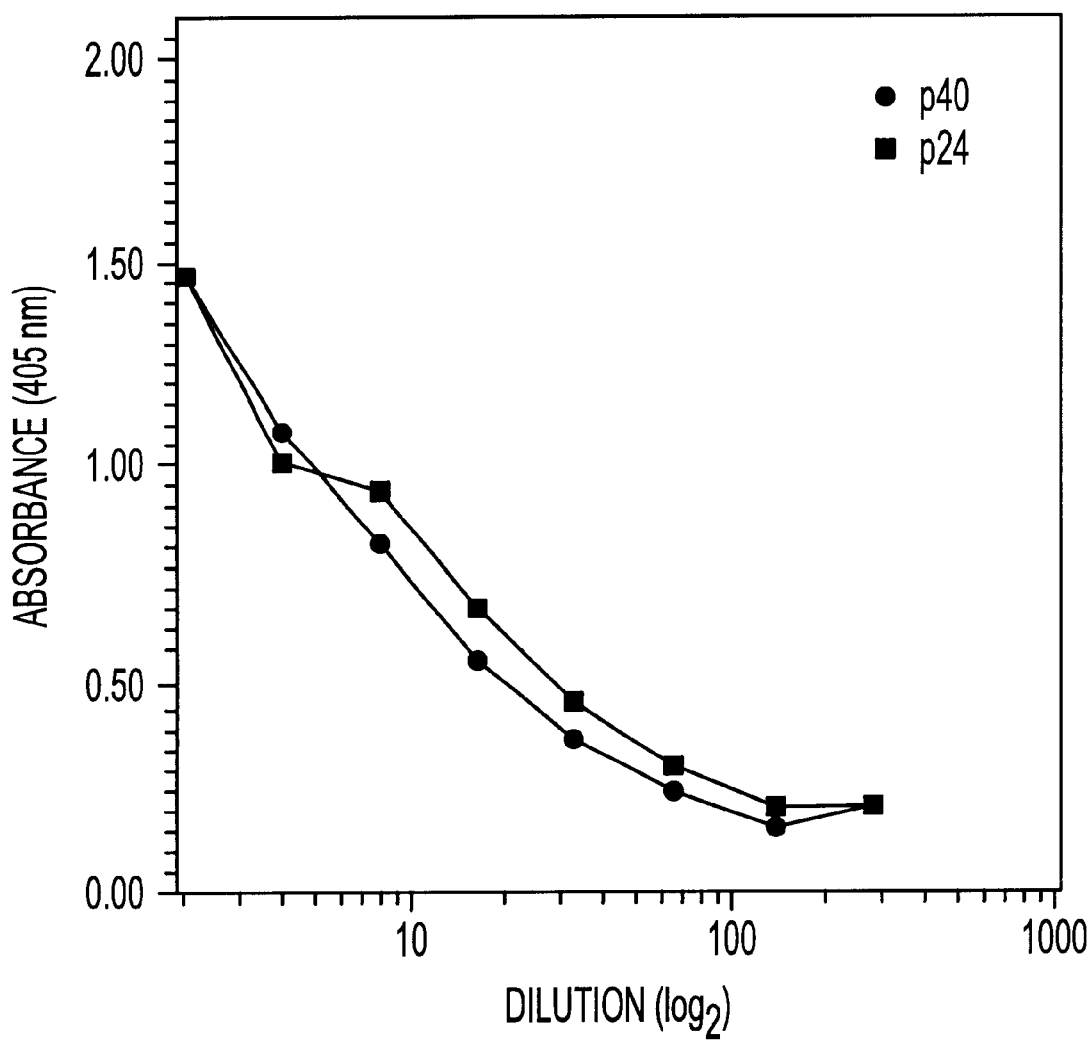
FIG. 4b shows CSF specimen 137—major depressive disorder, second episode, female, 29 years.
Figure 4C:
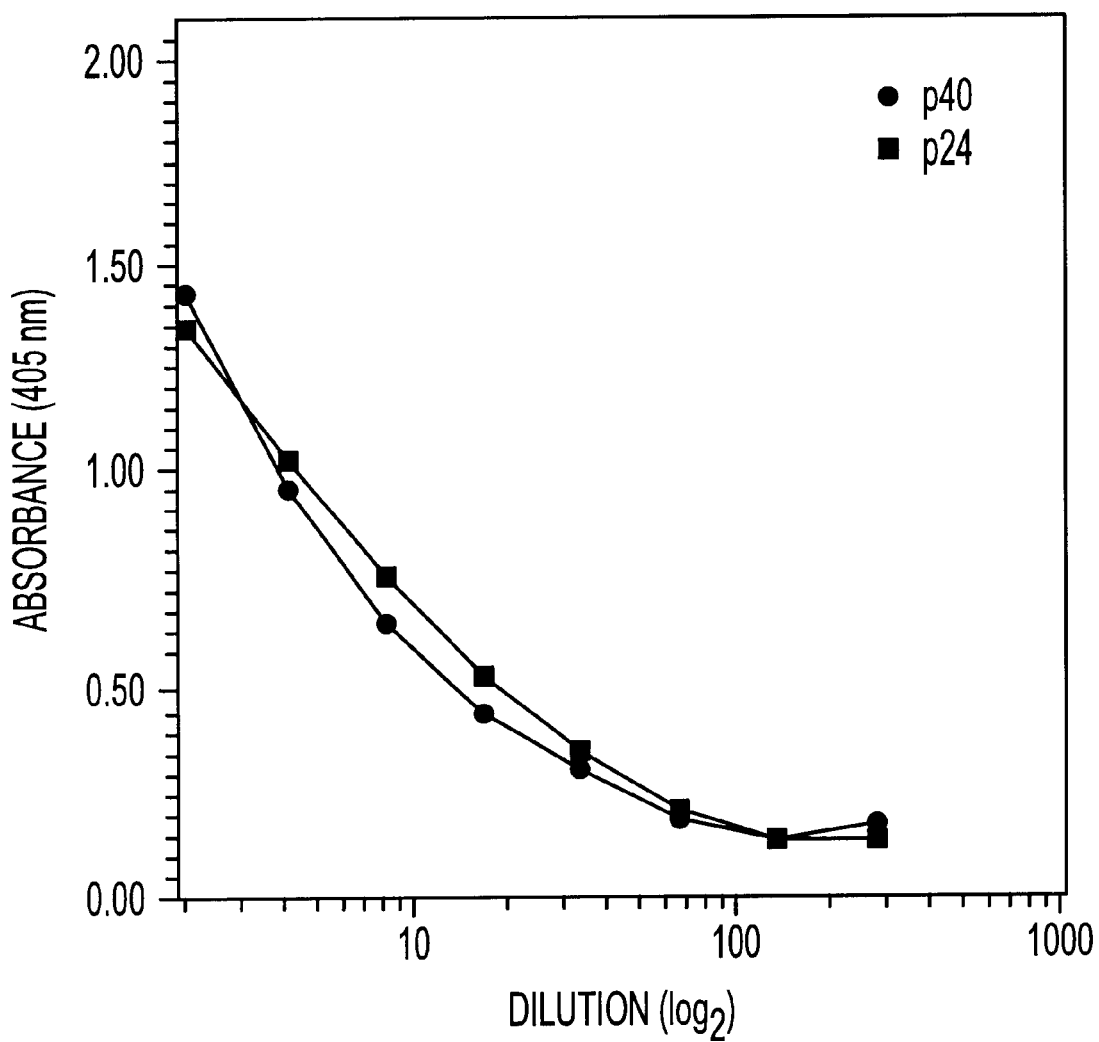
FIG. 4c shows another CSF specimen.
Figure 4D:
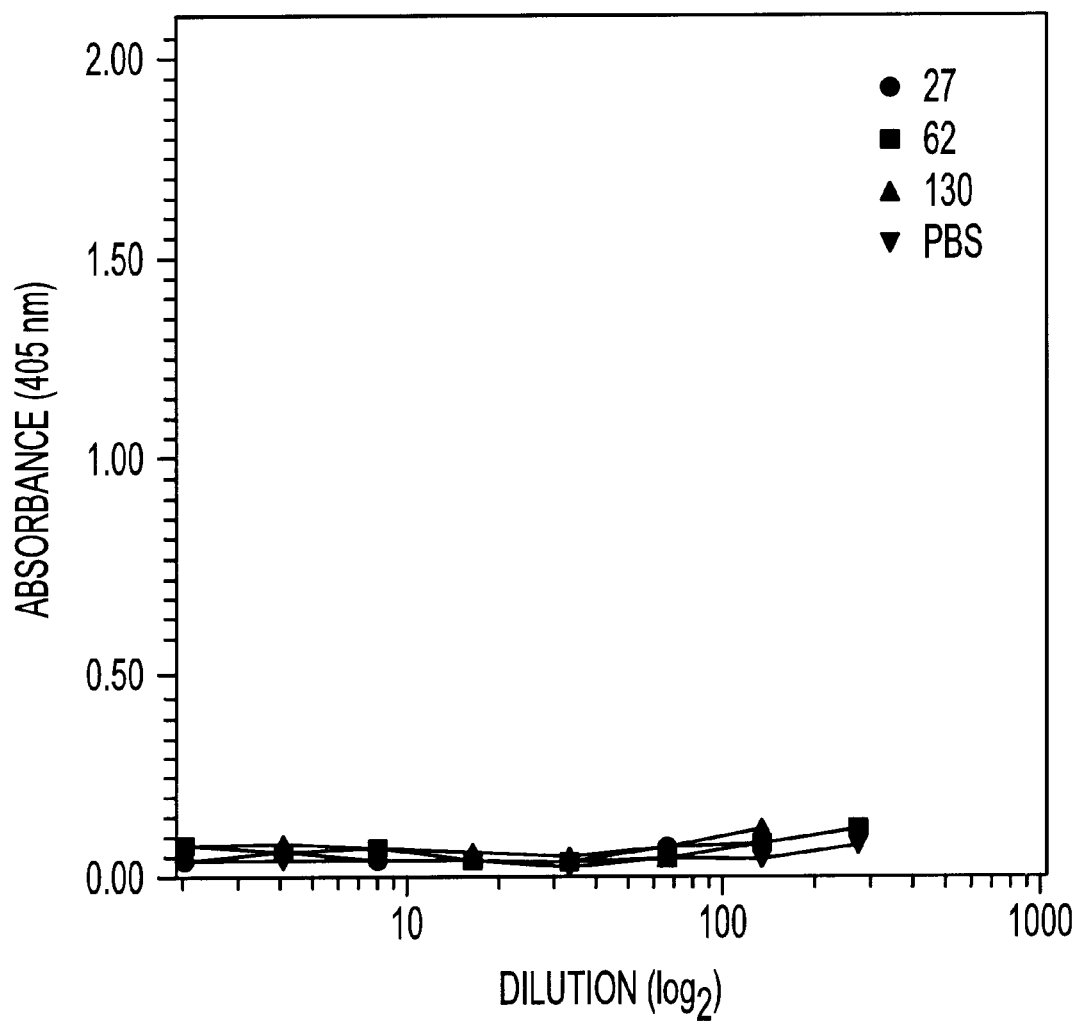
FIG. 4d shows CSF specimens from schizophrenia patients.

Finally, FIGS. 4a) to d) shows various results for CSF specimens in various dilutions. FIGS. a) to c) show a high level of positive antigen markers in affective disorders and d) shows negative assay results in schizophrenics.

The high values suggest a temporarily copious virus replication in the brain during the acute depression.

The individual figures show:

Figure a: CSF specimen from patient 36—major depressive disorder, second episode, female, 58 years Figure b: CSF specimen patient 137—major depressive disorder, second episode, female, 29 years Figure d: CSF specimens patient 27: schizophrenia, paranoid type, chronic, male, 39 years; patient 62: schizophrenia, paranoid type, unspecific, female, 37 years; patient 130: schizophrenia, paranoid type, subchronic, female, 20 years X. Summary Borna disease virus (BDV) is considered to be the prototype of a new family of coated negative-strand RNA viruses. BDV infects nerve cells, but also non-neuronal cells in the brain and the body without destroying the cells. BDV infections persist. They are found in humans and a large number of domestic animals and livestock. Human BDV infections are highly likely to play a role in periodic emotional disorders; in animals, BDV causes periodic behavioral disorders. Individual risk factors decide on the frequency at which the latent infection is activated and thus on the disease risk. Symptom-free carriers exist in all species. The diagnosis is made difficult by low viral replication rates and long latent phases.

The invention allows Borna disease virus (BDV) infections in humans and animals to be identified virtually completely by combining a newly-discovered assay parameter, CICs in the blood plasma, with parameters which are already known, viz. AG in leukocytes or blood plasma and Ab in the plasma. All three parameters can be determined on a single blood specimen (10 ml citrated blood).

The detection, described for the first time in the invention, of BDV-specific CICs as the only long-term persisting infection markers, allows not only healthy carriers (latent infections) to be identified, but also the course of the infection and the success of the therapy to be assessed in the case of diseased individuals.

What is claimed is:

1. A process for detecting Borna disease virus (BDV) infection in an animal, comprising (a) contacting a body fluid specimen with a first antibody specific for a circulating immune complex (CIC) indicative of BDV infection, which immune complex comprises a BDV antigen and an antibody to BDV antigen, and (b) detecting binding between said first antibody and said immune complex, wherein said binding is indicative of infection.

2. A process according to claim 1, additionally comprising detecting the presence of at least one BDV antigen in said body fluid specimen, by using a second antibody originating from a species different from said first antibody, wherein said second antibody is BDV-specific.

3. A process according to claim 2, wherein said BDV antigen is BDV nucleoprotein p40 or BDV-phosphoprotein p24.

4. A process according to claim 1, additionally comprising detecting the presence of at least one BDV antibody in said body fluid specimen, by binding a standardized solution of native BDV antigens, prepared from infected tissue culture or from brain of infected animals, to said first antibody, wherein said at least one BDV antibody is indicative of BDV infection and can be detected in said body fluid specimen.

5. A process according to claim 2, additionally comprising detecting the presence of at least one BDV antibody in said body fluid specimen, by binding a standardized solution of native BDV antigens, prepared from infected tissue culture or from brain of infected animals, to said first antibody, wherein said at least one BDV antibody is indicative of BDV infection and can be detected in said body fluid specimen.

6. A process according to claim 1, wherein said body fluid specimen is a blood, urine or spinal fluid specimen.

7. A process according to claim 2, wherein the body fluid specimen is a blood plasma, urine or spinal fluid specimen.

8. A process according to claim 2, wherein the body fluid specimen is a blood specimen, and wherein the antigen detection is carried out on a leukocyte fraction or on a blood plasma fraction of said blood specimen.

9. A process according to claim 7, wherein all tests are carried out on a blood plasma specimen.

10. A process for detecting a BVD circulating immune complex (CIC) of an antigen and an antibody which circulates in a body fluid, comprising:

(1) contacting a specimen of said body fluid with a support, wherein said support has monoclonal or polyclonal antibodies that bind to an antigen in said CIC, said monoclonal or polyclonal antibodies being fixed to said support via the Fc region wherein said monoclonal antibodies are monoclonal BDV-specific antibodies that are directed against native BDV antigens, and wherein said native BDV antigens are derived from natural sources;

(2) contacting said specimen from (1) with a secondary antibody of a species other than the assayed species, wherein said secondary antibody is specific for antibodies of the species whose body fluid specimen was used; and (3) detecting binding of said secondary antibody to said support.

11. A process according to claim 10, wherein the BDV-specific antibodies are selected from the group consisting of N protein-specific antibodies and P protein-specific antibodies.

12. A process according to claim 10, wherein the support is an adsorptively fixing polymer assay plate, which is first occupied as completely as possible with secondary antibodies which are specific for the species from which the immune complex-antigen-specific antibodies were obtained, and subsequently the immune complex-antigen-specific antibodies are applied to this layer of secondary antibodies.

13. A process according to claim 10, wherein detection of the secondary antibody in accordance with (3) of the process is done via an EIA or RIA process.

14. A process according to claim 13, wherein the secondary antibody is coupled to alkaline phosphatase and is visualized with p-nitrophenyl phosphate by means of a color reaction or made selectable by means of optical detectors.

15. A diagnostic kit for detecting BDV infection, comprising at least one BDV-specific monoclonal or polyclonal antibody, means for contacting these antibodies with a specimen suspected of containing BDV antigens or BDV immune complexes, and means for detecting the attached antigens or immune complexes.

16. A diagnostic kit for detecting BDV infection, comprising at least one BDV-specific monoclonal or polyclonal antibody occupied by a BDV antigen, means for contacting the antigen-occupied antibodies with a specimen suspected of containing BDV antibodies, and means for detecting the attached antibodies.

17. A diagnostic kit according to claim 15, comprising a unit on or in which the BDV-specific antibodies are present in immobilized form.

18. A diagnostic kit according to claim 17, wherein the BDV-specific antibodies are monoclonal or polyclonal antibodies obtained from a first species which are immobilized on a support coated with a species II-anti-species I IgG obtained from a second, different species.

19. A diagnostic kit according to claim 18, wherein the support is a solid plate or an assay tube.

20. A diagnostic kit according to claim 18, wherein the antibodies from the first species are polyclonal or monoclonal mouse antibodies.

21. A diagnostic kit according to claim 20, wherein the antibodies from the first species are selected from the group consisting of P-protein and N-protein specific monoclonal mouse antibodies, and the adsorptive coating of the support is composed of an anti-mouse IgG.

22. A diagnostic kit according to claim 21, wherein the anti-mouse IgG is a goat-anti-mouse IgG.

23. A diagnostic kit according to claim 18, wherein the BDV-specific antibodies are immobilized via polystyrene-bound C1q.

24. The process of claim 1, wherein said animal is human.

25. The process of claim 24, wherein said human is suffering from a neurological condition.

26. The process of claim 25, wherein said neurological condition is selected from the group consisting of depression, and obsessive-compulsive disorder.

* * * * *

UNITED STATES PATENT AND TRADEMARK OFFICE
CERTIFICATE OF CORRECTION

PATENT NO.     : 6,403,301 B1
DATED          : June 11, 2002
INVENTOR(S)    : Hans Ludwig and Liv Bode It is certified that error appears in the above-identified patent and that said Letters Patent is hereby corrected as shown below:

Drawings,
Please substitute Fig. 1 with Fig. 1 as shown below therefor.

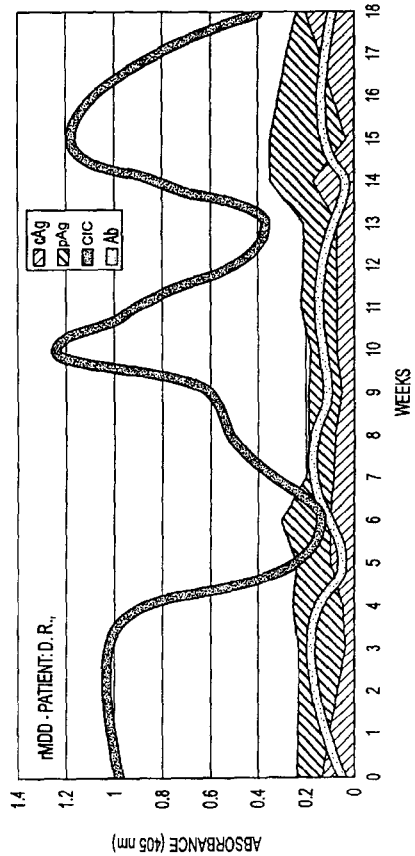

FIG. 1

UNITED STATES PATENT AND TRADEMARK OFFICE
CERTIFICATE OF CORRECTION

PATENT NO.   : 6,403,301 B1
DATED        : June 11, 2002
INVENTOR(S)  : Hans Ludwig and Liv Bode It is certified that error appears in the above-identified patent and that said Letters Patent is hereby corrected as shown below:

Drawings (cont'd),
Please substitute Fig. 2 with Fig. 2 as shown below therefor.

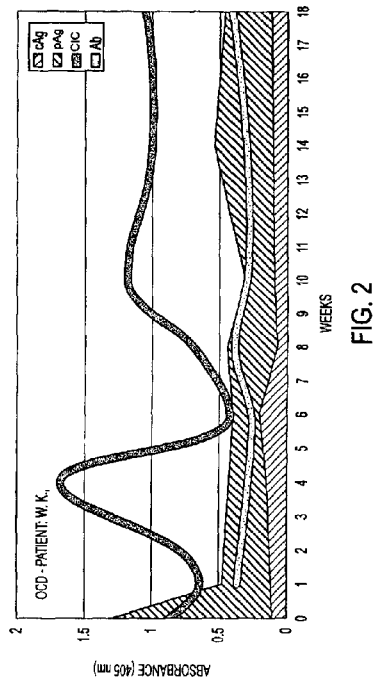

Signed and Sealed this

Seventeenth Day of December, 2002

JAMES E. ROGAN
*Director of the United States Patent and Trademark Office*